United States Patent [19]

Karanewsky

[11] Patent Number: 5,436,245
[45] Date of Patent: Jul. 25, 1995

[54] PHOSPHATE SUBSTITUTED AMINO OR IMINO ACIDS USEFUL AS ANTIHYPERTENSIVES

[75] Inventor: Donald S. Karanewsky, West Windsor, N.J.

[73] Assignee: E. R. Squibb & Sons, Inc., Princeton, N.J.

[21] Appl. No.: 153,500

[22] Filed: Nov. 17, 1993

Related U.S. Application Data

[63] Continuation of Ser. No. 896,912, Jun. 11, 1992, abandoned, which is a continuation of Ser. No. 396,170, Aug. 21, 1989, abandoned.

[51] Int. Cl.$^6$ ............... A61K 31/665; A61K 31/675; C07F 9/58; C07F 9/655
[52] U.S. Cl. ........................ 514/89; 514/80; 514/94; 514/95; 514/99; 514/100; 514/119; 540/476; 540/542; 546/21; 546/22; 546/23; 548/113; 548/119; 548/414; 558/170; 558/174; 549/6; 549/216; 549/218; 549/220
[58] Field of Search ............ 546/21, 22; 558/174, 558/170; 549/220; 514/89, 100, 119

[56] References Cited

U.S. PATENT DOCUMENTS

| | | | |
|---|---|---|---|
| 4,053,651 | 10/1977 | Ondetti et al. | 514/562 |
| 4,105,776 | 8/1978 | Ondetti et al. | 514/423 |
| 4,129,566 | 12/1978 | Ondetti | 546/326 |
| 4,151,172 | 4/1979 | Ondetti et al. | 548/413 |
| 4,154,935 | 5/1979 | Ondetti et al. | 546/189 |
| 4,168,267 | 9/1979 | Petrillo | 548/413 |
| 4,192,878 | 3/1980 | Ondetti | 514/365 |
| 4,199,512 | 4/1988 | Ondetti et al. | 548/455 |
| 4,217,359 | 8/1980 | Krapcho | 514/422 |
| 4,234,489 | 11/1980 | Ondetti et al. | 548/519 |
| 4,310,461 | 1/1982 | Krapcho et al. | 548/532 |
| 4,316,896 | 2/1982 | Thorsett et al. | 514/80 |
| 4,316,905 | 2/1982 | Krapcho | 514/343 |
| 4,432,972 | 2/1984 | Karanewsky et al. | 514/80 |
| 4,616,005 | 10/1986 | Karanewski et al. | 514/80 |
| 4,670,422 | 6/1987 | Karanewsky et al. | 524/80 |
| 4,963,539 | 10/1990 | Delaney | 514/119 |
| 5,102,875 | 4/1992 | Karanewsky | 514/80 |

FOREIGN PATENT DOCUMENTS

| | | |
|---|---|---|
| 868532 | 10/1978 | Belgium . |
| 2932021 | 2/1980 | Germany . |
| 7909246 | 12/1979 | Netherlands . |
| 2027025 | 2/1980 | United Kingdom . |

OTHER PUBLICATIONS

Karanewsky et al, *J. Med. Chem.,* p. 1459 (1990).
Stanton et al., J. Med. Chem. 26 (1983), 1267–1277.
Karanewsky et al., Journal of Medicinal Chemistry, 1988, vol. 31, No. 1, pp. 204 to 212.
Thorsett et al., Proc. Natl. Acad. Sci. 79, 2176–2180 (1982).

*Primary Examiner*—Emily Bernhardt
*Attorney, Agent, or Firm*—Timothy J. Gaul

[57] ABSTRACT

Hypotensive activity is exhibited by new phosphonate substituted amino or imino acids of the formula

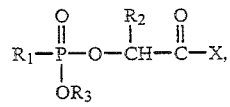

isomeric mixtures thereof and pharmaceutically acceptable salts thereof, wherein:
X is an imino or amino acid of the formula

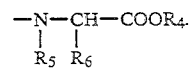

5 Claims, No Drawings

PHOSPHATE SUBSTITUTED AMINO OR IMINO ACIDS USEFUL AS ANTIHYPERTENSIVES

This is a continuation of U.S. Ser. No. 07/896,912, filed Jun. 11, 1992 (now abandoned), which is a continuation of U.S. Ser. No. 07/396,170, filed Aug. 21, 1989 (also abandoned).

BRIEF DESCRIPTION OF THE INVENTION

This invention is directed to new phosphonate substituted amino or imino acids of the formula

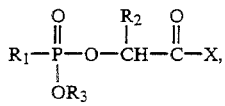

isomeric mixtures thereof and pharmaceutically acceptable salts thereof, wherein in formula I and throughout this specification, the symbols are defined as follows:

X is an imino or amino acid of the formula

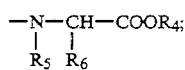

$R_1$ is alkyl of 1 to 10 carbons, aminoalkyl, haloalkyl,

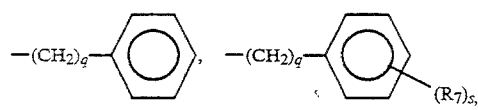

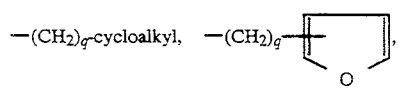

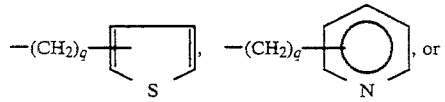

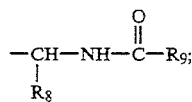

$R_2$ is hydrogen, lower alkyl, halo substituted lower alkyl,

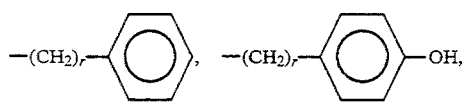

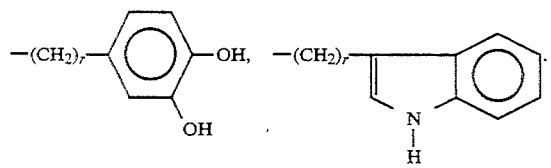

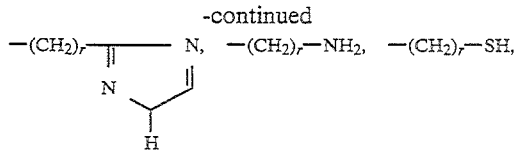

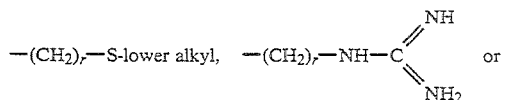

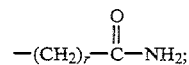

$R_3$ and $R_4$ are independently selected from hydrogen, lower alkyl, benzyl, alkali metal such as Li, Na or K, benzhydryl, or

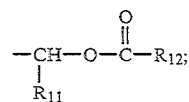

$R_5$ is

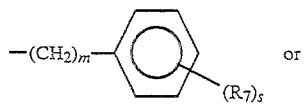

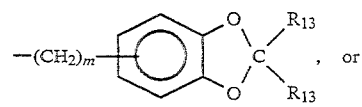

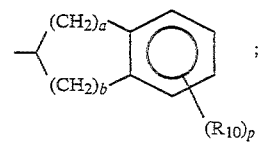

$R_6$ is hydrogen, lower alkyl,

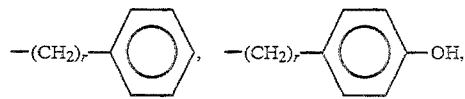

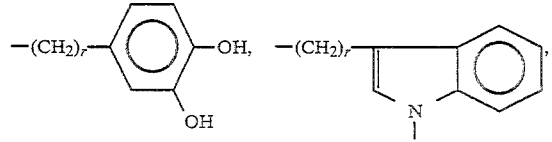

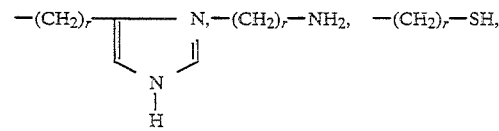

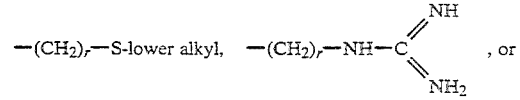

-continued $$-(CH_2)_r-\overset{\overset{O}{\|}}{C}-NH_2;$$

$R_7$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_8$ and $R_9$ are independently selected from hydrogen, lower alkyl, halo-substituted lower alkyl,

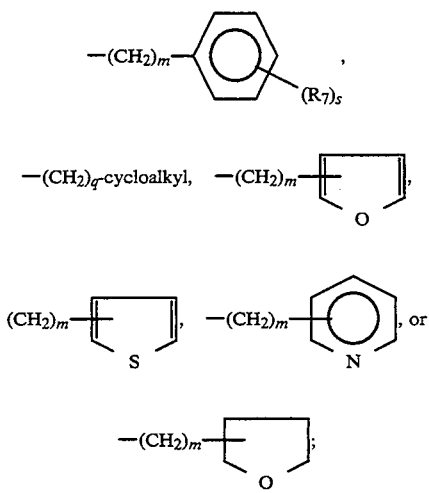

$R_{10}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

$R_{11}$ is hydrogen, lower alkyl, cycloalkyl, or phenyl, and $R_{12}$ is hydrogen, lower alkyl, lower alkoxy, phenyl, or $R_{11}$ and $R_{12}$ taken together are $-(CH_2)_2-$, $-(CH_2)_3-$, $-CH=CH-$, or

$R_{13}$ is hydrogen or lower alkyl;
$a+b=2$ or 3;
m is zero, one, two or three;
p is one, two or three, provided that p is more than one only if $R_{10}$ is hydrogen, methyl, methoxy, chloro, or fluoro;
q is an integer from 0 to 7;
r is an integer from 1 to 4; and
s is one, two, or three provided that s is more than one only if $R_7$ is methyl, methoxy, chloro or fluoro.

This invention in its broadest aspects relates to the phosphonate substituted imino or amino acid compounds of formula I above, to compositions containing such compounds and to the method of using such compounds as anti-hypertensive agents.

DETAILED DESCRIPTION OF THE INVENTION

Definition of Terms

The following definitions apply to the terms as they are used throughout this specification, unless otherwise limited in specific instances.

The term "alkyl" refers to straight or branched chain hydrocarbon groups having up to ten carbons, for example, methyl, ethyl, propyl, isopropyl, butyl, isobutyl, t-butyl, pentyl, isopentyl, heptyl, octyl, decyl, etc. The term "lower alkyl" refers to straight or branched chain groups having up to seven carbons. The preferred lower alkyl groups have up to four carbons with methyl and ethyl most preferred. Similarly, the terms "lower alkoxy" and "lower alkylthio" refer to such lower alkyl groups attached to an oxygen or sulfur.

The term "cycloalkyl" refers to saturated rings of 3 to 7 carbon atoms, with cyclopentyl and cyclohexyl being most preferred.

The terms "halo" and "halogen" refer to fluorine, chlorine, and bromine.

The term "halo-substituted lower alkyl" refers to such lower alkyl groups described above in which one or more hydrogens have been replaced by chloro, fluoro, or bromo groups, such as trifluoromethyl (which is preferred) pentafluoroethyl, 2,2,2-trichloroethyl, chloromethyl, bromomethyl, etc. Similarly, the term "amino-substituted lower alkyl" refers to lower alkyl groups in which one or more hydrogens have been replaced by $-NH_2$, i.e., aminomethyl, 2-aminoethyl, etc.

The compounds of this invention wherein at least one of $R_3$ or $R_4$ is hydrogen form basic salts with various inorganic and organic bases which are also within the scope of the invention. Such salts include ammonium salts, alkali metal salts such as lithium, sodium and potassium salts (which are preferred), alkaline earth metal salts such as calcium and magnesium salts, salts with organic bases (e.g., dicyclohexylamine salt), benzathine, N-methyl-D-glucamine, hydrabamine salts, and salts with amino acids such as arginine, lysine and the like. The nontoxic, physiologically acceptable salts are preferred, although other salts are also useful, for example, in isolating or purifying the products. The salts are formed using conventional techniques. All of the foregoing are within the meaning of the term "pharmaceutically acceptable salts."

The amino or imino acid or ester portion of the molecule of the products of formula I represented by X is in the L-configuration. Depending upon the definitions of $R_2$ and $R_8$, other asymmetric centers may be present in the phosphonyl sidechain. Thus, some of the compounds can exist in diastereoisomeric forms or in mixtures thereof. The above-described processes can utilize racemates, enantiomers or diastereomers as starting materials. When products containing only a single diastereomer are preferred, they can be separated by conventional chromatographic or fractional crystallization methods. The products of formula I wherein the imino acid ring is monosubstituted give rise to cis-trans isomerism. All of the foregoing are within the meaning of the term "isomeric mixtures."

Process of Preparation

The compounds of formula I wherein $R_1$ is other than

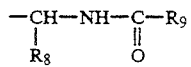

are prepared according to the following procedures. A phosphonic acid of formula

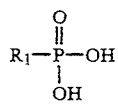

is treated with a chlorinating agent (e.g., phosphorus pentachloride) in the presence of an inert organic solvent (e.g., benzene) to form a compound of the formula

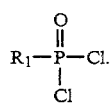

Compound III is reacted with a lactate of the formula

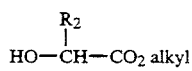

in the presence of an organic base (e.g., triethylamine) followed by an alcohol ROH (where $R_3$ is lower alkyl, benzyl, or benzhydryl) to form a compound of the formula

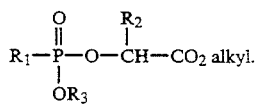

The formula V compound is then treated with strong base (e.g., sodium hydroxide or lithium hydroxide) in a mixture of water and an organic solvent (e.g., dioxane) to form the corresponding acid

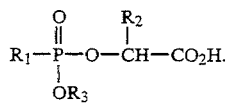

The acid VI or its activated form is then coupled with an imino or amino acid or ester of the formula VII

H—X.

The term "activated form" refers to the conversion of the acid to a mixed anhydride, symmetrical anhydride, acid chloride, or activated ester; see *Methoden der Organischen Chemie* (Houben-Weyl), Vol. XV, part II, page 1 et seq. (1974) for a review of the methods of acylation. Preferably, the reaction is performed in the presence of a coupling agent such as 1,1-carbonyldiimidazole, thionyl chloride, or dicyclohexylcarbodiimide.

In the above reaction, if $R_2$ is

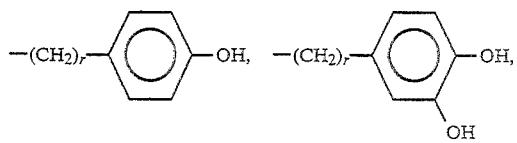

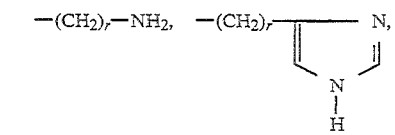

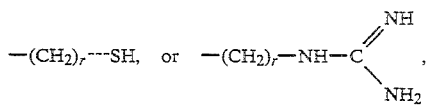

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Similarly, if in the above reaction $R_1$ is aminoalkyl, then the amino group should be similarly protected, preferably by phthalidyl. The protecting group is removed by treatment with hydrazine following completion of the reaction.

The products of formula I wherein $R_3$ or $R_4$ is hydrogen can be derived by hydrogenating those products wherein either or both of $R_3$ and $R_4$ are benzyl, or benzhydryl. Such hydrogenation can be effected, for example, by treatment with hydrogen in the presence of a palladium on carbon catalyst. Products in which $R_3$ and/or $R_4$ are alkyl can be converted to products in which $R_3$ and $R_4$ are hydrogen by chemical treatment, such as with sodium hydroxide in aqueous dioxane or trimethylsilylbromide in dichloromethane.

The ester products of formula I wherein $R_4$ is

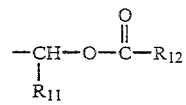

may be obtained by employing the imino or amino acid of formula V in the above reactions with the ester group already in place. Such ester reactants can be prepared by treating peptide, imino, or amino acids with an acid chloride such as

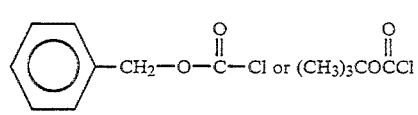

so as to protect the N-atom. The protected acid compound is then reacted in the presence of base with a compound of the formula

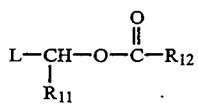  VIII wherein L is a leaving group such as chlorine, bromine, tolysulfonyloxy, etc., followed by removal of N-protecting group (e.g., by treatment with acid or hydrogenation).

The ester products of formula I wherein $R_4$ is

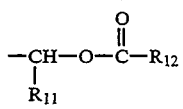

can also be obtained by treating the product of formula I wherein $R_4$ is hydrogen with a molar equivalent of the compound of formula VIII. The diester products wherein $R_3$ and $R_4$ are the same and are

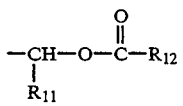

can be obtained by treating the product of formula I wherein $R_3$ and $R_4$ are both hydrogen or an alkali metal salt with two or more equivalents of the compound of formula VIII.

The ester products of formula I wherein $R_3$ is

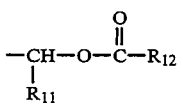

can be obtained by treating the product of formula I wherein $R_3$ is hydrogen or an alkali metal salt and $R_4$ is benzyl or benzhydryl with the compound of formula VIII in the presence of base. Removal of the $R_4$ ester group (e.g., by hydrogenation) yields the products of formula I wherein $R_3$ is

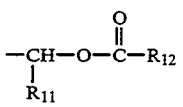

and $R_4$ is hydrogen.

The various imino and amino acids and esters of formula V are described in the literature and in the various patents referred to above. Various substituted prolines are also disclosed by Mauger et al., *Chem. Review*, Vol. 66, p. 46–86 (1966). When the amino or imino acid is known, it can be readily converted to the ester by conventional means. For example, the esters wherein $R_4$ is t-butyl can be obtained by treating the corresponding N-carbobenzyloxyimino acid with isobutylene under acidic conditions and then removing the N-carbobenzyloxy protecting group by catalytic hydrogenation. The esters wherein $R_4$ is benzyl can be obtained by treating the imino acid with benzyl alcohol and thionyl chloride.

The compounds of formula I wherein $R_1$ is

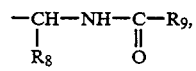

that is

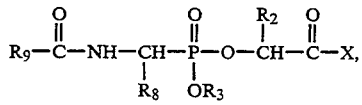  XIII may be prepared by reacting an aminophosphonic acid of the formula

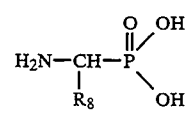  XIV with an acid chloride having the formula

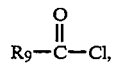  XV such as benzoyl chloride, in the presence of an inert organic solvent (e.g., dioxane) and a weak organic base (e.g., triethylamine) to yield

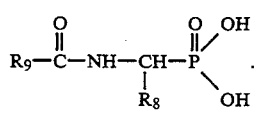  XVI

The formula XVI compound is then coupled with an imino or amino acid or ester of formula XVII

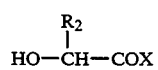  XVII in the presence of a coupling agent (e.g., dicyclohexylcarbodiimide) as described above to form

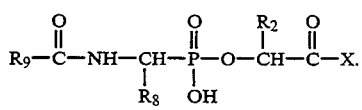  XVIII

Where X includes a protecting group, it may be removed by (1) hydrogenation where the protecting group is phenylmethoxycarbonyl or by (2) treatment with hydrazine where the protecting group is phthalidyl, to yield the compounds of formula XIII.

The compounds of formula XVII may be prepared by coupling a hydroxy acid of formula

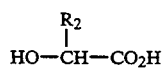  XIX as the free acid or corresponding sodium salt with an imino or amino ester of formula VII, preferably in the presence of a coupling agent such as diphenyl phosphorylazide.

Preferred Moieties

Preferred compounds of this invention with respect to the amino or imino acid or ester part of the structure of formula I are those wherein the symbols are defined as follows.

$R_6$ is hydrogen, lower alkyl of 1 to 4 carbons,

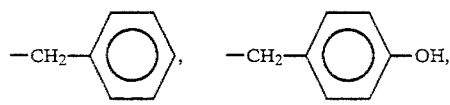

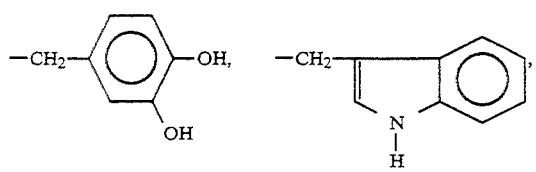

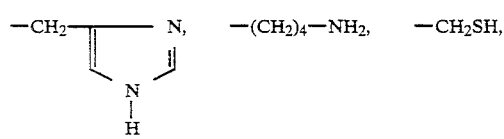

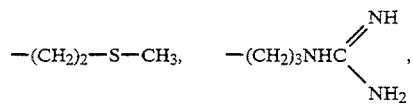

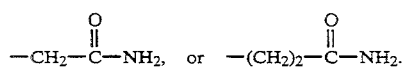

$R_4$ is hydrogen, an alkali metal salt, or

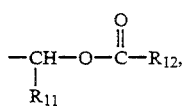

wherein
$R_{11}$ is hydrogen, methyl or isopropyl and $R_{12}$ is straight or branched chain lower alkyl of 1 to 4 carbons or phenyl.

Preferred compounds of this invention with respect to the phosphonyl sidechain of the structure of formula I are those wherein:
$R_2$ is hydrogen, lower alkyl of 1 to 4 carbons, amino-substituted lower alkyl, guanidino-substituted lower alkyl or $CF_3$;
$R_3$ is hydrogen, an alkali metal salt, lower alkyl of 1 to 4 carbons or

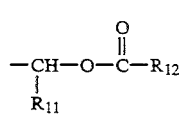

wherein $R_{11}$ is hydrogen, methyl or isopropyl and $R_{12}$ is hydrogen or straight or branched chain lower alkyl of 1 to 4 carbons or phenyl, especially hydrogen, alkali metal salt, ethyl,

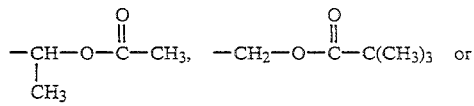

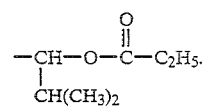

$R_1$ is alkyl of 1 to 10 carbons;

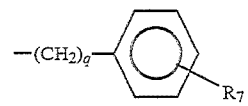

wherein q is an integer from 0 to 5 and $R_7$ is methyl, methoxy, methylthio, chloro, bromo, fluoro, or hydroxy; —$(CH_2)_q$—cycloalkyl wherein cycloalkyl is of 5 or 6 carbons and q is zero, one or two;

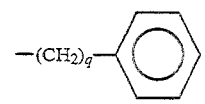

wherein q is an integer from 0 to 5;

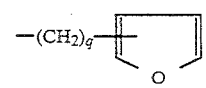

wherein q is an integer from 0 to 5;

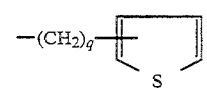

wherein q is an integer from 0 to 5;

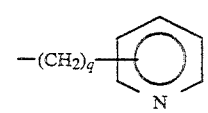

wherein q is an integer from 0 to 5; or

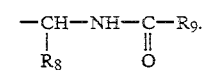

$R_8$ and $R_9$ are independently selected from lower alkyl of 1 to 4 carbons or

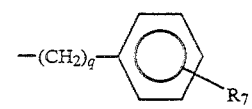

wherein q is an integer from 0 to 5 and $R_7$ is hydrogen, methyl, methoxy, methylthio, chloro, bromo, fluoro, or hydroxy, especially wherein $R_8$ is phenylethyl and $R_9$ is phenyl.

Use and Utility

The compounds of formula I, and the pharmaceutically acceptable salts thereof, are hypotensive agents. They inhibit the conversion of the decapeptide angiotensin I to angiotensin II and, therefore, are useful in reducing or relieving angiotensin-related hypertension. The action of the enzyme renin on angiotensinogen, a psuedo-globulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus, by the administration of a composition containing one (or a combination) of the compounds of this invention, angiotensin-dependent hypertension in a species of mammal (e.g., humans) suffering therefrom is alleviated. A single dose, or preferably two to four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dose of about 30 to 600 mg (preferably about 30 to 330 mg) of a compound of this invention, and about 15 to 300 mg (preferably about 15 to 200 mg) of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, tricynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with a physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

Specific Embodiments

The following working examples are illustrative and present preferred embodiments of the invention. Preparation of intermediate compounds appears just below the names of intermediate compounds. The intermediate prepared in part A of a working example will be referred to as "compound A" or "intermediate A" as a shorthand reference, and likewise for compounds prepared in parts B, C, D, etc. Except where otherwise indicated, all temperatures are in degrees Celsius.

EXAMPLE 1

N-[(S)-6-Amino-2-[[hydroxy(4-phenylbutyl)phosphinyl]oxy]-1-oxohexyl]-N-(2,3-dihydro-1H-inden-2-yl)glycine, dilithium salt A. N-(2,3-Dihydro-1H-inden-2-yl)glycine, phenylmethyl ester A stirred, cooled (to 0° C. in an ice bath) mixture of 2-aminoindan.hydrochloride (3.0 g, 0.018 mol) and triethylamine (4.9 ml, 0.035 mol) in dry ethyl ether (20 ml) was treated dropwise with an ethereal solution of benzylbromoacetate (2.55 ml, 0.016.1 mol in 10 ml ethyl ether). After completed bromide addition, the suspension was stirred overnight under argon at room temperature. After the suspension was filtered, the filtrate was evaporated, taken up in the ethyl acetate, washed with saturated sodium bicarbonate and water and brine, dried over anhydrous sodium sulfate, and evaporated to a brown oil. The crude oil was purified by flash chromatography on LPS-1 silica gel, eluting with 1:1 ethyl ether:hexanes. Product fractions were evaporated to a clear oil which was dissolved in ethyl ether (15 ml) and added by pipette portions to a hydrochloric acid saturated ethyl ether solution (75 ml) maintained at 0° C. The precipitated salt was collected by filtration, rinsed with ethyl ether and dried in vacuo to give 2.272 g (45%) of a benzyl ester (intermediate A) as a granular, white, hydrochloride salt with consistent $C^{13}$ NMR (CD$_3$OD, 15 MHz) spectral data. $R_f$=0.17, UV+PMA.

B.

(S)-2-[[Hydroxy(4-phenylbutyl)phosphinyl]oxy]-6-[[(phenylmethoxy)carbonyl]amino]hexanoic acid This compound was prepared as described in United States Patent No. 4,616,005, Example 137, parts A through G.

C.

N-(2,3-Dihydro-1H-inden-2-yl)-N-[(S)-2-[[hydroxy(4-phenylbutyl)phosphinyl]oxy]-6-[[(phenylmethoxy)carbonyl]amino]-1-oxohexyl]-glycine, phenylmethyl ester A mixture of intermediate A (474 mg, 0.0015 mol) and phosphonic acid B (549 mg, 0.0012 mol) in dry tetrahydrofuran (8 ml) and triethylamine (230 μl, 0.0015 mol) was treated with dicyclohexylcarbodiimide (833 mg, 0.004 mol) and the white suspension was stirred overnight under argon. The mixture was diluted with ethyl acetate and water, filtered, the organic phase washed with 5% potassium bisulfate, saturated sodium bicarbonate, filtered, washed with brine, dried over anhydrous sodium sulfate and evaporated to an oil plus residual dicyclohexylurea. The crude oil was purified by chromatography on a 2 cm pad of LPS-1 silica gel eluting with neat methylene chloride, 95:5 methylene chloride:Acetone, and 95:1:1 methylene chloride:methanol:acetic acid. Product fractions were evaporated, taken up in ethyl acetate, washed with 1.0N hydrochloric acid and brine, dried over anhydrous sodium sulfate and evaporated to a yellow oil. The oil was dissolved in ethyl acetate, treated with a small amount of activated charcoal, filtered and evaporated to give 583 mg (69%) of a phosphonic di-ester (intermediate C) as a pale yellow oil with consistent $C^{13}$ NMR spectral data (CDCl₃, 15 MHz).

Thin layer chromatography: (7:2:1) iPrOH-ammonium hydroxide-water. $R_f$=0.76, UV+PMA.

D.

N-[(S)-6-Amino-2-[[hydroxy(4-phenylbutyl)phosphinyl]oxy]-1-oxohexyl]-N-(2,3-dihydro-1H-inden-2-yl)glycine, dilithium salt 20% palladium on charcoal (87 mg, 15% by weight) was added to an argon-purged solution of the di-ester intermediate C (583 mg) in methanol (10 ml) and the black suspension was stirred under H₂ for 45 minutes. The catalyst was removed by filtration through dry, packed "Celite" and the filtrate evaporated. The residue was taken up in 1.0N lithium hydroxide (4 ml), diluted with water, filtered through a polycarbonate membrane and evaporated. The residue was dissolved in water and chromatographed on HP-20 resin, eluting with a neat water, neat acetonitrile linear gradient. Product fractions were evaporated, taken up in water (50 ml), filtered through a polycarbonate membrane, frozen, and lyophilized to give 341 mg (77% based on a hydrate of 2.4 moles water, molecular weight=571.68) of Example 1 as a fluffy white di-lithium salt.

Thin layer chromatography: (7:2:1) iPrOH-ammonium hydroxide-water, $R_f$=0.33, UV+PMA. Microanalysis for $C_{27}H_{35}N_2O_6P \cdot Li_2 + 2.4$ moles H₂O: Calculated: C, 56.70; H, 7.02; N, 4.90; P, 5.41 Found: C, 56.70; H, 6.69; N, 4.82; P, 5.40

EXAMPLES 2 to 8

The following compounds were prepared by the methods used in Example 1.

$$R_1-\underset{\underset{OH}{|}}{\overset{\overset{O}{\|}}{P}}-O-\underset{}{\overset{R_2}{|}}-\overset{\overset{O}{\|}}{C}-\underset{\underset{R_5}{|}}{N}-\underset{\underset{R_6}{|}}{C}-COO-R_4$$

| No. | R₁ | R₂ | R₄ | R₅ | R₆ |
|---|---|---|---|---|---|
| 2 | Ph—(CH₂)₄— | —(CH₂)₄—NH₂ | H | —CH₂—C₆H₄—OCH₃ | H |
| 3 | Ph—(CH₂)₄— | —(CH₂)₄—NH₂ | CH₂CH₃ | tetrahydronaphthyl | CH₃ |
| 4 | cyclohexyl—(CH₂)₃— | —(CH₂)₄—CH₃ | H | methoxy-indanyl (OCH₃) | CH(CH₃)₂ |
| 5 | CH₃—(CH₂)₅— | —(CH₂)₃—Ph | H | —CH₂—(benzodioxol-yl) | H |
| 6 | Ph—(CH₂)₂— | —(CH₂)₄—NH₂ | CH₃ | indan-2-yl | H |
| 7 | CH₃—(CH₂)₇— | —(CH₂)₄—NH₂ | H | —CH₂—(2,3-dichlorophenyl) | CH₃ |
| 8 | Ph—(CH₂)₅— | CH₃ | H | —(CH₂)₂—(3,4-dimethoxyphenyl) | H |

EXAMPLE 9

(S)-[[6-Amino-2-[[hydroxy(4-phenylbutyl)phosphinyl]oxy]-1-oxohexyl](3,4-dimethoxyphenyl)amino]acetic acid, dilithium salt A. (3,4-Dimethoxyphenylamino)acetic acid, methyl ester 4-Aminoveratrole (5.6 g, 0.37 mole), methylbromoacetate (4.6 g, 0.03 mole) and triethylamine (3.0 g, 0.03 mole) were dissolved in 40 ml of dry tetrahydrofuran and stirred under argon overnight. The black reaction mixture was concentrated in vacuo, dissolved in ethylacetate and stirred with 4 g of activated charcoal for 1 hour. This solution was filtered through a pad of silica (LPS-1) and the filtrate was evaporated to yield product as a tan solid with consistent $^{13}C$ spectral data (CD$_3$CN, 15 MHz).

Melting point 61°–64° C. R$_f$ 0.4 (1:1 Acetone-Hexane).

B.

(S)-2-(Acetyloxy)-6-[[(phenylmethoxy)carbonyl]amino]hexanoic acid

To a solution of (S)-6-[[(phenylmethoxy)carbonyl]amino]-2-hydroxyhexanoic acid (prepared as described in U.S. Pat. No. 4,616,005, Example 137, part B) (5.62 g, 0.0 mmol) in dry tetrahydrofuran (40 ml) at 0° C. (ice bath) under argon was added triethylamine (5.6 ml, 40.0 mmol) and acetyl chloride (2.84 ml, 40.0 mmole) and the resulting mixture stirred at 0° C. for 2 hours. The suspension was filtered, cooled to 0° C., treated with half saturated NaHCO$_3$ (40 ml) and stirred at 0° C. for 1 hour. The mixture was partitioned between ethyl acetate and 5% KHSO$_4$, the organic phase washed with saturated NaCl, dried over anhydrous Na$_2$SO$_4$ and concentrated in vacuo to give 8.20 g of crude acid as a yellow oil.

The crude acid was purified by conversion to its 1-adamantanamine salt. Thus, the crude acid was taken up in ethyl ether (25 ml) and treated with a solution of 1-adamantanamine (3.00 g, 19.8 mmol) in ethyl ether (20 ml). The resulting white precipitate was collected, washed with ethyl ether, and dried in vacuo to give adamantanamine salt (8.53 g, 90% overall) as a white solid.

To regenerate the free acid, the salt (8.53 g) was partitioned between ethyl acetate and 1N HCl, the organic phase washed with 1N HCl (2×30 ml) and saturated NaCl, dried over Na$_2$SO$_4$ and evaporated to give pure intermediate B (5.80 g, 91%) as a colorless, viscous oil:

Thin layer chromatography (CH$_2$Cl$_2$/MeOH/AcOH, 20:1:1) R$_f$ 0.82; $^{13}$C NMR (CD$_3$OD) δ22.6, 24.3, 27.9, 33.5, 36.6, 40.2, 56.0 (CH$_3$), 71.2 (CH), 115.8 (C), 126.6 (CH), 129.3 (CH), 130.5 (CH), 136.4 (CH), 143.6 (C), 160.8 (C), 174.5 (C).

C.

(S)-[[2-(Acetyloxy)-1-oxo-6-[[phenylmethoxy)-carbonyl]amino]hexyl](3,4-dimethoxyphenyl)-amino]acetic acid, methyl ester To a solution of acetate ester, intermediate B (1.29 g, 4 mmole) in 10 ml of tetrahydrofuran at 0° C. was added triethylamine (0.61 ml, 4.4 mmole), pivaloylchloride (0.54 ml, 4.4 mmole) and dimethylaminopyridine (0.2 g) and stirred at 0° C. for 2 hours. Intermediate A (0.98 g, 4.4 mmole) was added and the reaction mixture was stirred at room temperature under argon overnight. To drive the reaction to completion, 4 ml of pyridine was added. The resulting solution was stirred an additional 24 hours, evaporated, and the resulting residue was partitioned between ethyl acetate and 1N hydrochloric acid. The organic phase was washed with brine, dried (magnesium sulfate), and concentrated in vacuo. The residue was chromatographed on silica LPS-1 (150 g) using a 3:7 Acetone:Hexane solvent system. The appropriate fractions were evaporated to yield 0.67 g (32.5%) of intermediate C with consistent $^{13}$C spectral data (CD$_3$CN, 15 MHz).

D.

(S)-[[2-Hydroxy-1-oxo-6-[[(phenylmethoxy)-carbonyl]amino]hexy](3,4-dimethoxyphenyl)-amino]acetic acid, diphenylmethyl ester The N-phenylglycine derivative intermediate C (0.67 g, 1.3 mmole) was stirred with 7 ml 1N lithium hydroxide and 7 ml of dioxane for 1 hour. The reaction mixture was diluted with 200 ml ethyl acetate and washed with 10% potassium bisulfate, water, brine, dried (magnesium sulfate) and concentrated to 40 ml. Diphenyldiazomethane (0.5 g, 2.6 mmole) was added and the reaction mixture was stirred for 48 hours under argon, concentrated to 10 ml and chromatographed on 600 ml LPS-1 silica using a 7:3 ethyl acetate:Hexane solvent system. The appropriate fractions were combined and concentrated in vacuo to yield 0.61 g (73.5%) of intermediate D with consistent $^{13}$C spectral data (CD$_3$CN, 15 MHz).

E.

(S)-[[(2-Hydroxy-4-phenylbutylphosphinyl)oxy]-1-oxo-6-[[(phenylmethoxy)carbonyl]amino]-hexyl](3,4-dimethoxyphenyl)amino]acetic acid, diphenylmethyl ester Phenylbutyl phosphonous acid (0.2 g, 1 mmole), and intermediate D (0.61 g, 0.96 mmole) were dissolved in 4 ml of tetrahydrofuran at 0° C. under argon. Dicyclohexylcarbodiimide (0.21 g, 1 mmole) and dimethylaminopyridine (0.1 g) were added and the reaction was stirred at room temperature for 4 hours. Because no reaction was indicated by thin layer chromatography, 4 ml of pyridine was added and the reaction mixture was stirred at 40° C. for 3 hours and at room temperature overnight. After addition of 250 ml of ethyl acetate, the solution was filtered, washed with 5% potassium bisulfate, saturated sodium bicarbonate, water, and brine. It was concentrated in vacuo and theoretical yield of product was assumed.

The resulting phenylbutyl phosphonous acid ester was dissolved in 5 ml of dioxane and added to a 5 ml water solution of sodium metaperiodate (0.22 g). This was stirred under argon overnight, diluted with ethyl acetate and washed with 1% sodium bisulfite, water, 5% potassium bisulfate, water, and brine. The organic phase was dried and concentrated in vacuo to yield crude intermediate E. This compound was partially purified by preparation of its adamantamine salt in ether-hexane. The semisolid adamantamine salt of intermediate E was partitioned between ethyl acetate and 1N hydrochloric acid. The ethyl acetate solution was washed with water and brine, dried (magnesium sulfate) and concentrated in vacuo to yield 0.61 g of intermediate E with consistent $^{13}$C spectral data (CD$_3$CN, 15 MHz).

F.

(S)-[[6-Amino-2-[[hydroxy(4-phenylbutyl)phosphinyl]oxy]-1-oxohexyl](3,4-dimethoxyphenyl)-amino]acetic acid, dilithium salt Intermediate E (0.61 g) was hydrogenated in 10 ml of methanol using 20% palladium on charcoal as catalyst at 1 atmosphere of hydrogen gas pressure. After 45 minutes, the solution was filtered through "Celite" and concentrated in vacuo. The residue was dissolved in acetone:1N lithium hydroxide (PH 11.2) and chromatographed on 60 ml of HP-20 using 200 ml each of water, 5% acetone-water, and 10% acetone-water. The appropriate fractions were combined, concentrated in vacuo to 5 ml and filtered through millipore. The filtrate was lyophilized to yield 0.29 g of Example 4 as a white solid.

Melting point 185°-195° C. Analysis Calculated for $C_{26}H_{35}N_2PO_8Li_2$ L.1.35 water: C, 54.52; H,6.64; N,4.89; P,5.41. Found: C, 54.52; H,6.51; N,4.88; P,5.3.

EXAMPLE 10

[[(S)-6-Amino-2-[[hydroxy(4-phenylbutyl)phosphinyl]oxy]-1-oxohexyl](4-methoxyphenyl)amino]-acetic acid, dilithium salt A. (4-Methoxyphenyl)aminoacetic acid, ethyl ester p-Anisidine and ethyl bromoacetate were reacted according to the procedure given in Example 9, part A to give intermediate A as a light yellow solid in 68% yield.

Thin layer chromatography: $R_f=0.5$ 7:3 hexane/acetone.

B.

(S)-[[2-(Acetyloxy)-1-oxo-6-[[phenylmethoxy)-carbonyl]amino]hexyl](4-methoxyphenyl)amino]-acetic acid, ethyl ester Intermediate A and Intermediate B from Example 9 were reacted according to the procedure given in Example 9, part C to give intermediate B in 43% yield.

Thin layer chromatography: $R_f=0.9$ 7:3 hexane/actone.

C.

(S)-[[2-Hydroxy-1-oxo-6-[[(phenylmethoxy)-carbonyl]amino]hexyl](4-methoxyphenyl)amino]acetic acid, diphenylmethyl ester Intermediate B was reacted according to the procedure given in Example 9, part D to give intermediate C in 74% yield.

Thin layer chromatography: $R_f=0.15$ 2:5 hexane/ethyl acetate.

D.

(S)-[[(2-Hydroxy-4-phenylbutylphosphinyl)oxy]-1-oxo-6-[[(phenylmethoxy)carbonyl]amino]hexyl](4-methoxyphenyl)amino]acetic acid diphenylmethyl ester Intermediate C was reacted according to the procedure given in Example 9, part E to give intermediate D in 74% yield.

Thin layer chromatography: $(CH_2Cl_2/MeOH/AcOH, 20:1:1)$ $R_f=0.92$.

E.

[[(S)-6-Amino-2-[[hydroxy(4-phenylbutyl)phosphinyl]oxy]-1-oxohexyl](4-methoxyphenyl)amino ]-acetic acid, lithium salt Intermediate D was reacted according to the procedure given in Example 9, part F to give Example 10 as a white solid dilithium salt.

Analysis $C_{25}H_{33}N_2O_7PLi_2.1.2H_2O$: C,55.60; H,6.60; N,5.19; p,5.73. Found: C,55.59; H,6.58; N,5.14; P,5.50. $[\alpha]_D+63.6°$ (c=0.5, methanol).

EXAMPLES 11 to 16

The following compounds were prepared by the methods used in Example 9.

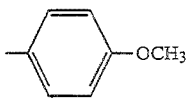

| No. | $R_1$ | $R_2$ | $R_4$ | $R_5$ | $R_6$ |
|---|---|---|---|---|---|
| 11 | Ph—(CH$_2$)$_2$— | —(CH$_2$)$_5$—NH$_2$ | H | 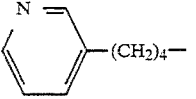 | H |
| 12 | 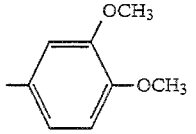 | —(CH$_2$)$_4$—CH$_3$ | H | 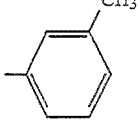 | CH(CH$_3$)$_2$ |
| 13 | CH$_3$—(CH$_2$)$_5$— | —(CH$_2$)$_3$—Ph | H | 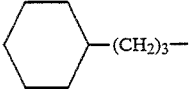 | H |
| 14 | 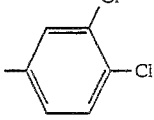 | —(CH$_2$)$_4$—NH$_2$ | H | | H |

-continued

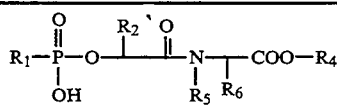

| No. | $R_1$ | $R_2$ | $R_4$ | $R_5$ | $R_6$ |
|---|---|---|---|---|---|
| 15 | $CH_3-(CH_2)_7-$ | $-(CH_2)_4-NH_2$ | H | 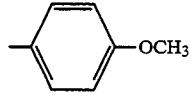 | $CH_3$ |
| 16 | $Ph-(CH_2)_5-$ | $CH_3$ | H | 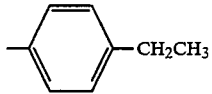 | H |

What is claimed is:

1. A compound of the formula

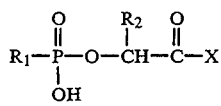

or pharmaceutically acceptable salts thereof, wherein:

X is $-\underset{R_5}{N}-\underset{R_6}{CH}-COOR_4$;

$R_1$ is alkyl of 1 to 10 carbons,

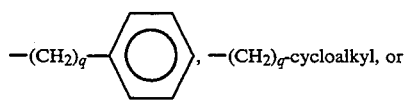

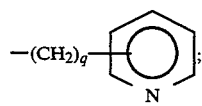

$R_2$ is hydrogen, lower alkyl,

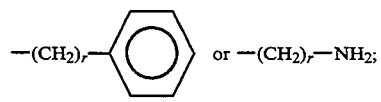

$R_4$ is hydrogen, lower alkyl, benzyl, or alkali metal;
$R_5$ is

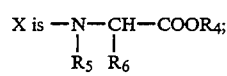

$R_6$ is hydrogen or lower alkyl;
m is zero, one, two or three;
q is an integer from zero to seven;
r is an integer from one to five;
"alkyl" refers to straight or branched chain groups having up to ten carbons;
"lower alkyl" refers to alkyl groups of 1 to 7 carbons; and
"cycloalkyl" refers to saturated rings of 3 to 7 carbons.

2. The compound of claim 1 wherein $R_1$, $R_2$, $R_4$, $R_5$, and $R_6$ are defined by the following table

| $R_1$ | $R_2$ | $R_4$ | $R_5$ | $R_6$ |
|---|---|---|---|---|
| $CH_3(CH_2)_5$ | $(CH_2)_3Ph$ | H | 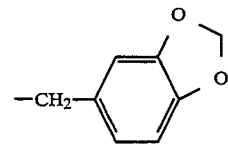 | H | wherein Ph is phenyl.

3. A composition useful for treating hypertension comprising a pharmaceutically acceptable carrier and an effective amount of a compound of claim 1.

4. The composition of claim 3 also including a diuretic.

5. A method of alleviating hypertension in a mammalian specie which comprises administering an effective amount of the compound of claim 1.

* * * * *